United States Patent [19]

Tateosian et al.

[11] Patent Number: 4,892,478

[45] Date of Patent: Jan. 9, 1990

[54] METHOD OF PREPARING DENTAL APPLIANCES

[75] Inventors: Louis H. Tateosian, York, Pa.; Louis C. Souder, Ocean City, N.J.

[73] Assignee: Dentsply Research & Development Corp., Milford, Del.

[21] Appl. No.: 171,493

[22] Filed: Mar. 21, 1988

[51] Int. Cl.[4] .................... A61C 13/00; A61C 13/01
[52] U.S. Cl. .......................... 433/6; 264/16; 433/7
[58] Field of Search .................. 264/16–19; 433/6, 7, 34–36

[56] References Cited

U.S. PATENT DOCUMENTS

| | | | |
|---|---|---|---|
| 2,246,822 | 6/1941 | van Rossem | 264/16 |
| 2,799,054 | 7/1957 | van Rossem | 264/16 |
| 3,218,374 | 11/1965 | Perbohner et al. | 264/17 |
| 3,987,545 | 10/1976 | Kennedy | 433/36 |
| 4,028,808 | 6/1977 | Schwaptz | 433/7 |
| 4,054,996 | 10/1977 | Wallshein | 433/7 |
| 4,071,424 | 1/1978 | Dart et al. | |
| 4,080,736 | 3/1978 | Kennedy | 433/36 |
| 4,195,047 | 3/1980 | Drennan et al. | 264/225 X |
| 4,299,568 | 11/1981 | Crowley | 433/6 |
| 4,351,853 | 9/1982 | Jochum et al. | |
| 4,432,730 | 2/1984 | Gettleman et al. | 264/17 X |
| 4,439,380 | 3/1984 | Michl et al. | 264/16 |
| 4,468,196 | 8/1984 | Keller | 433/7 X |
| 4,504,225 | 3/1985 | Toshi | 433/6 |
| 4,516,936 | 5/1985 | Hulsink | 433/6 |
| 4,533,326 | 8/1985 | Anthony | |
| 4,543,063 | 9/1985 | Cohen | |
| 4,551,486 | 11/1985 | Tateosian et al. | |
| 4,568,558 | 2/1986 | Angrick et al. | |
| 4,585,667 | 4/1986 | Hubner | |
| 4,615,665 | 10/1986 | Tateosian et al. | |
| 4,656,053 | 4/1987 | Angrick et al. | |
| 4,661,065 | 4/1987 | Gettleman et al. | 264/17 X |
| 4,689,015 | 8/1987 | Denyer et al. | |
| 4,746,469 | 5/1988 | Yamashita | 264/17 X |
| 4,752,222 | 6/1988 | Bass | 433/7 |

OTHER PUBLICATIONS

Abstract from Journal of Dental Research, vol. 66, Mar. 11–15, 1987.

*Primary Examiner*—Jan H. Silbaugh
*Assistant Examiner*—Karen D. Kutach
*Attorney, Agent, or Firm*—Edward J. Hanson, Jr.

[57] ABSTRACT

A method of producing dental appliances, especially orthodontic appliances, but also including dentures and other dental prosthesis. The method includes placing a self-merging dental gel especially as a stream on a dental cast and under and around preformed dental parts mounted on the cast and merging the dental gel into a homogeneous form of the complete part and then curing the formed dental appliance. The dental gel is a colloidal system including a hardenable dispersing medium, a colloid and a catalyst, preferably a photoinitiator.

4 Claims, 1 Drawing Sheet

METHOD OF PREPARING DENTAL APPLIANCES

The invention relates to a hardenable dental gel material for producing dental appliances and a method of producing dental appliances preferably orthodontic appliances, from a hardenable dental gel material.

BACKGROUND

Orthodontic appliances are used to correct malocclusions and anomalies of tooth position and to retain the dentition in the desired position after tooth movement until sufficient calcification has occurred to stabilize the tooth.

Orthodontic appliances have been prepared from acrylate- or methacrylate-based plastic in the past by the alternate application of powdered acrylate or methacrylate copolymers and monomers, particularly those comprising the lower methyl methacrylates, to plaster dental casts using a method referred to by those skilled in the art of orthodontic dental appliance construction as the "Salt and Pepper Method." After initial build up the formed orthodontic appliance is polymerized under pressure on its cast, for example in a pressure cooker, under water at 15-100 psi for 10-30 minutes Alternatively simple orthodontic appliances have been formed from polymer material by vacuum molding.

A method of orthodontic appliance construction is described in U.S. Pat. Nos. 4,568,558 and 4,656,053. The method described involves building up a plurality of resin layers on a plaster dental cast. This is done by applying a first thin layer of a composition of a diurethanedimethacrylate prepared from 2,2,4-trimethylhexamethylenediisocyanate and 2-hydroxyethylmethacrylate, and a photopolymerization catalyst to the plaster dental cast and briefly exposing this first thin layer to light whereby the thin layer is partially polymerized. Successive application of at least one additional thin layer on the first thin layer is carried out with partial polymerization of each successive thin layer by brief exposure to light until the thickness and shape desired for the device or appliance is attained, and the shaped partially polymerized material is subsequently polymerized completely by exposure to light.

A method for relining a denture at chairside is described in U.S. Pat. No. 4,543,063. The patent describes urethane elastomer compositions catalyzed with camphoroquinone and containing fillers such as colloidal silica. Also shown are acrylic compositions.

OBJECTS

It is an object of the invention to provide a method for producing orthodontic appliances that enables the body portion of the orthodontic appliance to be placed and shaped in a single continuous placement procedure not unlike what might be described as an open mold injection forming of the material that will form the body portion.

It is a further object of the invention to provide a hardenable dental gel material that is fluid enough to be hand extruded and flowable about at least most of the conventional preplaced, preformed orthodontic appliance parts without displacing or distorting the preformed parts while having slump and flow properties that retain desired contours upon placement and merging flow properties allowing substantially full homogeneity and freedom from occluded porosity throughout the hardenable dental gel when the hardenable dental gel is placed from a nozzle.

It is an additional object of the invention to provide a method for producing orthodontic appliances that will save significant time over all presently known procedures and produce orthodontic appliances of equal or superior properties.

Yet a further object of the invention is to provide an orthodontic appliance having substantial structural homogeneity, providing good strength and tending to reduce delamination (there are no unnecessary plies) and cracking which can allow penetration of fluids and micro organisms resulting in mouth odor and also tending to induce stress regions.

Another object of the invention is to adapt the hardenable orthodontic dental gel to other dental applications and methods for producing dental appliances such as dental prosthesis.

SUMMARY OF THE INVENTION

By the present invention in one aspect a method of producing a dental appliance is provided that involves extruding a stream of self-merging hardenable dental gel onto a dental cast, and permitting the gel to take the shape of the cast and curing the gel to produce a hardened form of the dental appliance. The extrusion may be interrupted from time to time to enable repositioning of the nozzle and the like but the hardenable dental gel is not hardened during the continuing lay down or extrusion until the final form or shape of the dental appliance is attained. After completion of the form of the dental appliance and the substantial reaching of homogeneity by the substantially completed self-merging of the hardenable dental gel into a continuous homogeneous mass the hardenable dental gel is converted to a solid.

Preferably the method involves producing an orthodontic dental appliance form on a dental cast with at least one dental wire embedment portion extending above the dental cast and spaced approximately 0.05 mm from the surface of the cast. First dental gel is extruded between the dental cast and the wire embedment portion and about the wire embedment portion and thereafter the dental gel extrusion is continued further extending the dental gel to complete the form of the orthodontic dental appliance.

By other aspects of the invention a hardenable dental gel is provided that is a colloidal system comprising a dispersing medium, a colloid, and a catalyst. Preferably the hardenable dental gel has a viscosity of 8,000 to 50,000 cps, a slump of 15 mm to 27 mm and the dispersing medium comprises urethane diacrylate, the colloid is present in an amount of 0.5 to 20% by weight based on the total weight of the hardenable dental gel composition, and the catalyst is a photoinitiator.

By another aspect of the invention a method is provided for producing a dental appliance comprising placing a hardenable dental gel, containing a catalyst, and a colloidal system. The colloidal system includes a dispersing medium comprising polymerizable monomer and colloidal particulate. The method includes placing the hardenable dental gel against a model, and activating the catalyst to polymerize the monomer and change the colloidal system to a solid.

DRAWINGS

BEST MODE

GENERAL DESCRIPTION

Figure 1:
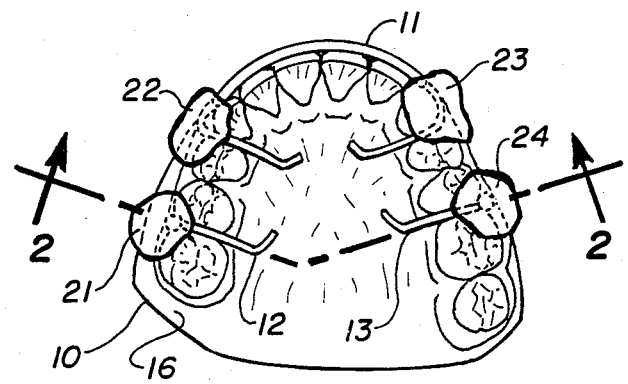
FIG. 1 is a plan view of a set-up orthodontic preassembly.
Figure 2:
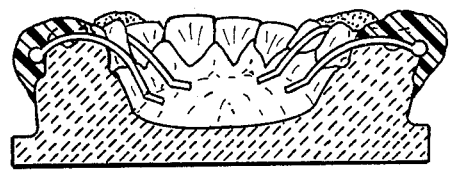
FIG. 2 is a section along line 2—2 of FIG. 1

By an aspect of the invention dental appliances, especially in one most preferred aspect, orthodontic appliances, are produced by applying to a dental cast a hardenable dental gel that will form a continuous structure of substantial homogeneity. This is expeditiously accomplished by extruding a hardenable dental gel having sufficient fluidity to easily flow about preplaced, preformed dental appliance parts without displacing or distorting the preformed dental appliance parts and needing no pressure means, beyond a minimal hand extrusion pressure from a collapsible container tube, to flow under preformed appliance wires or other substructure spaced only 0.3 mm from the dental cast surface and achieve good encapsulation of such wires or other parts. For expeditious application, the hardenable dental gel also has merging flow properties bringing about substantially full homogeneity where the extruded hardenable dental gel flows against already laid down extruded hardenable dental gel as it is extruded from a nozzle. Furthermore, for expeditious application, the hardenable dental gel's slump and flow properties should retain the extrudate in relative position for a sufficient time to enable completion of the appliance form so that the hardenable dental gel will not puddle or run down the slope of the dental cast but will form a generally uniform thickness throughout, even though applied to steeply inclined cast surfaces.

The hardenable dental gel may be used for making dental appliances other than orthodontic appliances. By orthodontic appliance it is meant orthodontic retainers and other orthodontic devices for the movement or protection of teeth and bony structure and including mouth guards and the like as contrasted to dental prosthesis such as dentures which provide artificial dentition or artificial teeth support and including the reconstruction of dentures and parts thereof and denture reline and the like. The present invention also includes, in some of its broader aspects, the preferred construction of dental prosthesis. The preferred use of the hardenable dental gel of this invention is in the preferred method of this invention which is constructing, preparing or manufacturing orthodontic dental appliances. Split orthodontic appliances are still considered to be included within the continuous structure definition.

DENTAL GEL

The preferred hardenable dental gel is a colloidal system i.e. an intimate mixture of two substances, one of which, called the dispersed phase (or colloid) is uniformly distributed in a finely divided state through the second substance, called the dispersion medium (or dispersing medium). The colloidal system has little three dimensional strength and is easily disrupted even by moderate stress. However, when the colloidal system is confronted by stress of very low order such as is encountered in sagging or leveling, the structure can offer considerable resistance to flow. In fact, if the stress is sufficiently low, the colloidal structure can completely block flow.

Having said this, it must be considered that especially for the preferred construction of orthodontic appliances where it is not practical in the usual instance to use spatulas or other tools to move or shape the hardenable dental gel, the hardenable dental gel must also have the property of substantially complete merging or flow together when two portions are laid down touching each other before curing without interruption. Generally the only manipulation that is practical is by moving the extrusion nozzle slightly forward to push the flow forward slightly while extruding the hardenable dental gel. The hardenable dental gels ted as a group to be tacky to work with and not accommodative of easy manipulation once placed. Two adjacent portions of gel are thus self-merging, by which it is meant, when in good contact with each other they will flow together and merge and substantially level so that to the unaided eye, certainly, there is no interface line, this does not mean that a depression may not be present on the surface where they have flowed together The flow together should be reasonably, rapid, prefereably occurring within seconds and certainly within a minute and well less than 5 minutes, in preferred embodiments.

The preferred dispersing medium is liquid and comprised of a monomer preferably having at least two cross linkable C-C (Carbon to Carbon) double bonds and being a non-gaseous addition polymerizable ethylenically unsaturated compound, having a boiling point above 100° C. at atmospheric pressure, a molecular weight of about 100–1500 and being capable of forming high molecular weight addition polymers readily. More preferably, the monomer is preferably an addition photopolymerizable polyethylenically unsaturated acrylic or methacrylic acid ester containing two or more acrylate or methacrylate groups per molecule or mixtures thereof. A few illustrative examples of such multifunctional acrylates are ethylene glycol diacrylate, ethylene glycol dimethacrylate, trimethylopropane triacrylate, trimethylopropane trimethacrylate, pentaerythritol tetraacrylate or pentaerythritol tetramethacrylate, 1,6-hexanediol dimethacrylate, and diethyleneglycol dimethacrylate.

More preferably, the monomer is a urethane diacrylate that is the Isocyanate free reaction products of organic polyisocyanates such as hexamethylene diisocyanate, isophorone diisocyanate or tolylene diisocyanate with hydroxyl group containing (meth) acrylates such as glycol monoacrylate, hydroxypropylmethacrylate or 1,4-butanediol monoacrylate.

Also useful in some special instances are monoacrylates such as n-butyl-acrylate, n-butyl methacrylate, 2-ethylhexyl acrylate, lauryl-acrylate, and 2-hydroxypropyl acrylate. Small quantities of amides of (meth)acrylic acid such as N-methylol methacrylamide butylether are also suitable, N-vinyl compounds such as N-vinyl pyrrolidone, vinyl esters of aliphatic monocarboxylic acids such as vinyl oleate, vinyl ethers of diols such as butanediol-1, 4-divinyl ether and allyl ether and allyl ester are also suitable Also included would be other monomers such as the reaction products of di- or polyepoxides such as butanediol-1, 4-diglycidyl ether or bisphenol A diglycidyl ether with (meth)acrylic acid. The characteristics of the photopolymerizable liquid dispersing medium can be modified for the specific purpose by a suitable selection of monomers or mixtures thereof.

The preferred colloid is fumed silica although other fumed and non-fumed finely divided colloidal materials can be used in proper circumstances with facility. The more preferred colloids are inorganic, and most preferably the inorganic oxides especially the fumed silicas. The fumed silicas can be silanized or unsilanized but the unsilanized are preferred.

Preferably the hardenable dental gel contains 0.5 to 20% by weight of colloid based on the total weight of the hardenable dental gel composition, more preferably 2 to 12% and most preferably 4 to 10%, for orthodontic appliances the colloid content should be more preferably 3 to 10%, most preferably 4 to 8%.

The third essential ingredient of the preferred colloidal system is a polymerization catalyst. Many catalyst are known for catalyzing C-C unsaturated monomers including heat activated and photoactivated catalyst such as the peroxides and ketones. The preferred catalysts are photopolymerization catalysts such as the ketones and even more preferably the alpha diketones, most preferably camphoroquinone.

In addition to the three essential ingredients of the preferred colloidal system other ingredients that are preferred in a more preferred colloidal system for some applications include photoaccelerators, diluents and silanes. Also useful in some applications are many other ingredients such as pigments, substantially non-swellable fillers, fibers, stabilizers, dyes, bonding agents, fluorescent agents, light refracting and reflecting agents and the like.

Preferably the hardenable dental gel has a viscosity of 8,000 to 50,000 cps at 20 RPMs, more preferably 10,000 to 40,000 cps and most preferably 15,000 to 35,000 cps, a slump of 8 mm to 40 mm and more preferably 10 mm to 25 mm and most preferably 15 mm to 30 mm and the dispersing medium comprises urethane diacrylate and the catalyst is a photoinitiator. By urethane diacrylate it is meant to include urethane dimethacrylate.

DENTAL APPLIANCE PREPARATION

The appliance preparation will be described with particular emphasis to the preferred orthodontic appliances and with reference to the Drawing where appropriate.

1. A gypsum dental cast of the patient's arch(s) or a portion thereof or of other structure in the oral cavity of a human patient is prepared in the normal manner.
2. When present, wires (such as 11, 12 and 13, FIG. 1), retainers, retentive mesh, or other preformed parts of the dental appliance that is being manufactured are formed in the normal manner and fitted/conformed to the dental cast according to normal procedures well known to those skilled in the art. Preferably, approximately an 0.5 mm space (in the usual situation between 0.3 and 0.8 mm) is provided between the embedment portions (FIG. 4, 14 and 15) of the preformed parts and the dental cast surface. The embedment portions of the preformed parts are the portions that are to be embedded in the hardenable dental gel as the retention portions to be retained in fixed relation to the finished dental appliance.
3. When the preformed portions that are to be used are metal, their embedment portions preferably are thoroughly cleaned by a cleaning agent to remove any grease or other contaminant. Suitable preferred cleaning agents for most situations are solvents such as methyl methacrylate liquid (monomer) or ethanol. The cleaning agent may be used by brushing on or dipping the embedment portions or rubbing them with a cloth in the presence of the cleaning solvents. The embedment portion of the cleaned preformed part may be coated with one of many polymer-metal bonding agents to enhance wetting and bonding. The cleaned preformed parts may then be laid aside until the dental cast is prepared for receipt of the hardenable dental gel when such procedure is necessary. Of course, in some instances it may be preferable to prepare the dental cast before cleaning the embedment portions.
4. In one preferred method, a model release agent is coated on the dental cast. Preferably the model release agent is applied in a thin layer or provided in a thin layer with any excess being wiped off. It is important in the usual instance not to have any excess of the model release agent in order to avoid contaminating the embedment portions and to maintain the preferred approximately 0.5 mm space between the preformed appliance embedment portions and the dental cast for assurance of good encapsulation of the embedment portions by the hardenable dental gel.
5. In one of the more preferred sequences of the preferred method, as the next step the wires or other preformed parts are positioned on the dental cast and secured, preferably with sticky wax, on the buccal/labial areas (as shown in FIG. 1 at 21, 22, 23 and 24) after completion of all of the above steps. It will be obvious to those skilled in the art that in some situations it may be preferable to vary the sequence of the steps.
6. The hardenable dental gel is extruded onto the model portions of the dental cast, which are those portions of the dental cast that provide the basic shape of the dental appliance in conformity to the anatomy of a dental patient. As used herein, the basic shape of the dental appliance or part being produced is the "form" of the dental appliance which may subsequently require correction, trimming, smoothing and polishing and the like. In the case of a denture, the model would be the soft tissue of the patient and the denture would be a preformed part. (As shown in FIGS. 3, 4 and 5 hardenable dental gel 25 is shown extruded from a nozzle 26 on a tube 27.)

Figure 3:
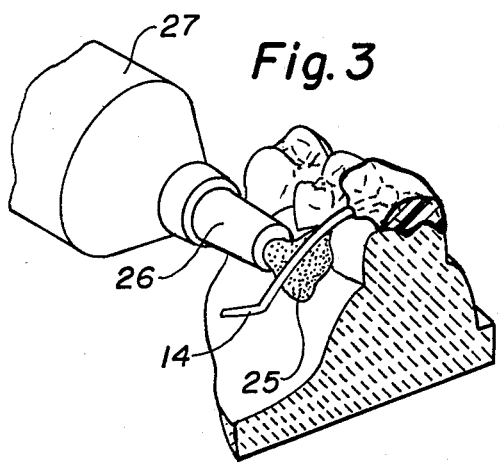
FIG. 3 is a broken away perspective of FIG. 1 showing an operation of the invention.
Figure 4:
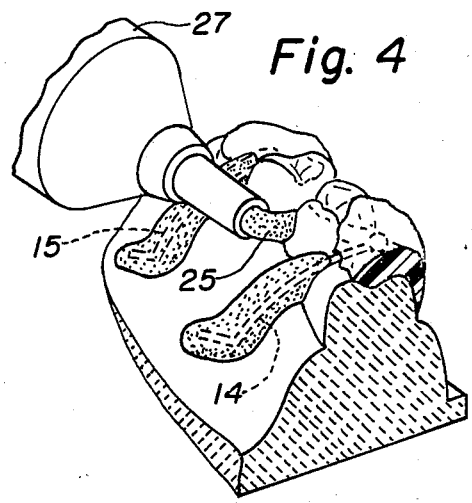
FIG. 4 is a broken away perspective of FIG. 1 showing a further operation of the invention.
Figure 5:
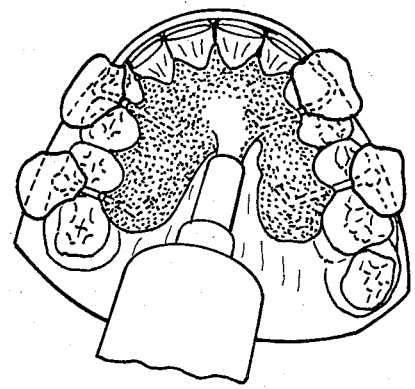
FIG. 5 is a plan view of FIG. 1 showing a further operation of the invention.

When wires or other preformed parts having embedment portions are present, the hardenable dental gel is preferably first extruded under and around the embedment portions (as illustrated in FIGS. 3 and 4) and thereafter preferably especially directed to flow into interproximal (as illustrated in FIG. 4) and other areas (as illustrated in FIG. 5) to complete the desired shape of the dental appliance. Preferably the hardenable dental gel should be applied in slight overbuild and extended for full area coverage and sufficient thickness to enable any necessary corrections to be made during the usual finishing procedures to save time and effort.

7. The hardenable dental gel is then hardened, preferably by polymerization to a solid. Preferably the polymerization is carried out via actinic light initiation, more preferably actinic light applied within the visible light range, about 360 to 600 nanometers. In the preferred curing or polymerization procedure, the hardenable dental gel is first cured on the dental cast and then removed and inspected.

If there are any imperfections such as voids, they can be repaired by adding additional hardenable dental gel at this time. The added hardenable dental gel should preferably be cured when repair is necessary.

8. Using many of the presently available polymerizable materials, it is preferable to treat the dental appliance at this stage to eliminate surface tac or stickiness and to assure cure of the side of the dental appliance that was against the dental cast and in some instances may be shaded from direct actinic light exposure by preformed appliance parts. Preferably all surfaces of the unfinished or rough formed dental appliance are coated with an air barrier coating and the back of the unfinished appliance is exposed to actinic light preferably by positioning the rough dental appliance in an inverted position. By rough dental appliance it is meant the hardened dental appliance that is to undergo finishing procedures.

9. The finishing of the dental appliance is then, in the most preferred sequence of the preferred method, carried out beginning with removal of the air barrier coating. This may be done in one preferred procedure by thoroughly washing with water while scrubbing with a brush.

10. The dental appliance, depending on the usual requirements, may then be preferably further finished in the normal manner to a polished surface using burs, pumice, tripoli, rag wheels, etc. The finishing procedures are typically the same as those used by orthodontic labs in making "Salt and Pepper" acrylic dental appliances from polymer powder and monomer liquids.

The invention is further illustrated by the following examples:

EXAMPLE 1

A. Preparation of light activator 1. 138.0 g (grams) glacial methacrylic acid and 8.0 g butylated hydroxytoluene were placed in an amber Nalgene bottle. After the butylated hydroxytoluene dissolved, the bottle was placed in the freezer for 15 minutes.
2. 276.0 g N,N-dimethylaminoethylneopentyl acrylate which had just been removed from the freezer, 98.0 g gamma-methacryloxypropyltrimethoxysilane and 80.0 g camphorquinone were added to the bottle. The bottle was placed on a shaker for 4 hours, until the camphorquinone dissolved.

B. Preparation of pigment suspension 0.8 g Chromophthal scarlet RS pigment (a product of Ciba Giegy) was suspended in 199.2 g 1,6 hexanediol dimethacrylate in an amber glass bottle.

C. Preparation of hardenable dental gel

1. A one gallon Ross mixer was heated to 52° C.
2. 945.0 g Mhoromer 666-0 (a product of Rohm Tech), was added to the mixing pot.
3. 19.0 g of the light activator prepared above was added.
4. The pigment suspension bottle described above was shaken and 6.0g was added to the mixer pot.
5. A 13 mm vacuum was drawn and the liquids were mixed at Speed #1 for 9 minutes and then Speed 2 ½ for 6 minutes.
6. The vacuum was released, and 30.0g of Aerosil 200 was added.
7. A 13 mm vacuum was drawn and the powder was deaerated for 15 minutes.
8. Mixing was resumed on Speed #1 for 1 minute and Speed 2 ½ for 9 minutes.
9. The mixer was stopped, the vacuum released, and the pot was opened.
10. The pot and blades were scraped down.
11. Mixing was continued at Speed 3 ½ under 13 mm vacuum for an additional 15 minutes.
12. The mixer was stopped and the material was placed in tubes and light-proof bottles.

The above mixing procedure was repeated with the compositions in Table I.

TABLE I

| Notebook Reference Composition | Example 1 | Example 2 | Example 3 | Example 4 | Example 5 | Example 6 | Example 7 |
|---|---|---|---|---|---|---|---|
| Urethane Dimethacrylate[1] | 94.50 | 93.50 | 92.50 | 93.50 | 92.50 | 93.10 | 84.50 |
| Gamma-methacryloxy propyltrimethoxy silane | .31 | .31 | .31 | .31 | .31 | .31 | .31 |
| N,N—Dimethylamino[5] ethyl neopentyl-acrylate | .87 | .87 | .87 | .87 | .87 | .87 | .87 |
| Methacrylic acid | .44 | .44 | .44 | .44 | .44 | .44 | .44 |
| Butylated hydroxytoluene | .03 | .03 | .03 | .03 | .03 | .03 | .03 |
| camphorquinone | .25 | .25 | .25 | .25 | .25 | .25 | .25 |
| 1,6 Hexanediol dimethacrylate | .60 | .60 | .60 | .60 | .60 |  | .60 |
| Pigments | .002 | .002 | .002 | .002 | .002 |  | .002 |
| Unsilanated Fumed[2] silica | 3.00 | 4.00 | 5.00 |  | 3.00 | 5.00 | 13.00 |
| Silanated Fumed silica[3] |  |  |  | 4.00 |  |  |  |
| Acrylic rubber[4] modifier |  |  |  |  |  | 2.00 |  |

All numbers are in percent by weight. 100.002 = 100% in Example 1.
[1]N,N—bis(2-methacryloxyethoxycarbonyl)-1,6 diamino-2,4,4-trimethyl hexane; a product of Rohm Tech
[2]Aerosil A-200, a product of DeGussa
[3]Aerosil R972, a product of DeGussa
[4]Acryloid KM334, a product of Rohm and Haas
[5]A product of Rohm Tec

D. Test sample preparation

1. Hardenable dental gels were loaded into stainless steel molds with 3 ×11 ×82 mm cavities, between clear copolymer films and pressed to express the excess material.
2. Next the molds were placed in a TRIAD® Curing Unit (a product of Dentsply the subject of U.S. Pat. No. 4,582,998) and the samples were cured with 10 minutes light irradiation on one side and 6 minutes on the other.
3. The samples were removed from the mold and finished with 120 then 400 grit SiC paper to 2.85 ×11 ×85 mm.

The samples were tested and the results are recorded in Table II.

TABLE II

|  | Hardenable Dental Gels Tested | | | | | | |
| --- | --- | --- | --- | --- | --- | --- | --- |
| Properties Tested | Example 1 | Example 2 | Example 3 | Example 4 | Example 5 | Example 6 | Example 7 |
| Flexural Strength (psi)[a] | 17,500 | 17,200 | 17,700 | 17,000 | 15,000 | 17,000 | 17,900 |
| Deflection at Break (mm)[a] | 10.5 | 11.6 | 13.3 | 14.7 | 12.8 | 14.3 | 10.2 |
| Elastic Modulus (psi)[a] | 507,000 | 502,000 | 507,000 | 484,000 | 433,000 | 512,000 | 500,000 |
| Izod Impact (ft.lb/in)[b] | 3.7 | 4.0 | 4.8 | 4.6 | 4.3 | 4.9 | 2.3 |

[a]ASTM D790
[b]ASTM D256

EXAMPLE 8

Determination of Slump On Hardenable Dental Gels

The following procedure was carried out under yellow light.

1. A glass plate was placed on a balance.
2. A tube of hardenable dental gel with a 3 mm orifice and 12 mm nozzle was held vertically over plate approximately ½" from surface. 1.00 ±0.05 grams of gel was squeezed out onto glass surface keeping gel in a circular form.
3. The hardenable dental gel was allowed to sit for 2 minutes.
4. The hardenable dental gel was cured for 40 seconds with a hand held dental curing light. (PRISMETICS® Light, a product of Dentsply International Inc.).
5. Cured hardenable dental gel was removed from glass plate and the bottom diameter of the cured material was measured in two directions 90° from each other. The average of these two readings was determined.

| Hardenable Dental Gel from Example Number: | 3 | 6 |
| --- | --- | --- |
| Slump Reading: | 23 ± 2 mm | 18.5 ± 1.5 mm |

EXAMPLE 9

Determination Of Viscosity Of Hardenable Dental Gel

A 5x NBT Wells-Brookfield Micro Viscometer was used for the determination of viscosity of the hardenable dental gels by the following method:

1. A small amount of the hardenable dental gel, sufficient to cover the outer edge and 1 mm up the spindle, was dispensed onto the spindle from a nasal tube with a 3 mm orifice and 12 mm nozzle.
2. Readings were obtained at 20 and 50 rpm speeds at 21° C.

The hardenable dental gel from Example 6 was tested:

|  | Speed | Reading | Cps |
| --- | --- | --- | --- |
| #1 | 20 | 12.5 | 24,500 |
| #2 | 20 | 10.1 | 19,900 |
|  | 50 | 21.6 | 17,000 |
| #1 | 20 | 16.1 | 31,500 |
|  | 50 | 32.5 | 25,600 |
| #2 | 20 | 14.6 | 28,100 |
|  | 50 | 25.5 | 20,100 |

EXAMPLE 10

ORTHODONTIC DENTAL APPLIANCE PREPARATION

1. Referring to the Drawing, referring to FIG. 1, gypsum dental cast 10 of the patient's upper arch was prepared in the normal manner by pouring gypsum (CASTONE® a product of Dentsply International Inc.) into a dental impression of a patients mouth.
2. A labial arch wire 11 and two ball clasps retainer wires 12 and 13 were formed from break resistant stainless steel 0.032 diameter wire to fit the dental cast in the normal manner and fitted/conformed to the dental cast according to normal procedure. The wires were formed so that their embedment portions were spaced approximately 0.5 mm from the dental cast surface 16.
3. The embedment portions were thoroughly cleaned with 190 proof ethanol. The cleaning agent was applied by rubbing with a cotton tack cloth saturated with the alcohol. The cleaned preformed portions were then laid aside while the dental cast was prepared for receipt of the dental gel.
4. A Model Release Agent (TRIAD® Model Release Agent a product of Dentsply International Inc.) was coated in a thin layer on the dental cast. The model release agent was then smoothed with the finger to assure that the coating was substantially thin and uniform.
5. Next the wires were positioned on the dental cast and secured with sticky wax on the buccal/labial areas 21, 22, 23 and 24.
6. Now with the preparation phase of the method complete, the hardenable dental gel of Example 6 was extruded under and around the embedment portions 14 and 15 (and others not shown) of the wires and then extruded toward and flowed into interproximal FIG. 4 and other areas FIG. 5, overbuilding and extending for complete area coverage and sufficient thickness.
7. The formed dental appliance was then placed in a light curing polymerization unit (TRIAD® II Curing Unit a product of Dentsply International Inc.) and processed for 3 minutes on the dental cast. The now rough dental appliance was then removed from the dental cast and inspected with the unaided eye and found to be free of any substantive imperfections. Next all surfaces were coated with an air barrier coating with a brush (Triad Air Barrier Coating a product of Dentsply International Inc.). The coated rough dental appliance was then placed back in the light curing unit in an inverted position and processed for 6 minutes off the dental cast.

8. Next the cured rough dental appliance was washed thoroughly with water, using a brush, to remove the air barrier coating.

9. The rough dental appliance was now ready for finishing. Finishing was accomplished by trimming away the expanded overbuilt portions while shaping to give esthetically pleasing contours and substantially matching opposed portions that would be visually pleasing to a patient. Carbide burs (FAS-KUT® burs - product of Dentsply International Inc.) were used for this purpose. The partially finished portions of the dental appliance formed from the dental gel were found to trim very easily without fracture or chipping of the dental appliance. The grinding was followed by smoothing-first using pumice and a rag wheel and then tripoly and a rag wheel in normal fashion. The dental appliance smoothed easily and well. The smoothing procedure was followed by the usual polishing of the dental appliance with a conventional wax based polishing agent followed by washing with soap and water using a brush. The appliance was observed with the unaided eye to have a high shine and give an excellent appearance and when repositioned on the dental cast had maintained its fit.

One of the important and preferred aspects of the invention is the hardenable dental gels characteristic of retaining substantially a uniform viscosity over a long period of time when stored at room temperature of 22° C. under light free conditions. This can be demonstrated by testing after thorough mixing and a delay of 10 minutes, 1 hour and one month. The viscosity has been observed to remain substantially constant. Thus, a test for preferred operation is to test at these intervals and maintain a viscosity constant reading within 30%, more preferably 20% and most preferably 10%. Thus if the viscosity reading was 10,000 cps it most preferably should remain within a range of 11,000 and 9,000 cps on a subsequent reading.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

It is claimed:

1. A method of preparing a dental appliance comprising the steps of
    (a) preparing a dental cast of a patients 'mouth,
    (b) adapting a dental appliance substructure to said dental cast,
    (c) placing said substructure on said dental cast,
    (d) extruding at least one stream of self-merging hardenable dental gel around said substructure and on said dental cast in adjacent extruded portions and permitting said adjacent extruded portions to merge together whereby there are no interface lines between said adjacent extruded portions, said gel comprising a colloidal system of a hardenable dispersing medium, a colloid, and a catalyst, and having a viscosity of 8000 to 50,000 cps at 20 RPM's and a slump of 10 mm to 27 mm, and
    (e) curing said gel in one step to produce a dental appliance without interface lines having a form adapted specifically for said patients'mouth.

2. The method of claim 1 wherein said dental appliance is an orthodontic dental appliance comprising the additional steps of
    (a) placing at least two preformed dental wire parts in spaced apart positions on said dental cast, each said wire part having an embedment portion which is held above a surface of said cast,
    (b) extruding said stream of hardenable gel between said dental cast and each said embedment portion and about said embedment portion, and
    (c) thereafter extending said stream of hardenable gel to complete a shape of said dental appliance.

3. The method of claim 1 which further comprises the steps of preparing said gel to have a viscosity of about 10,000 to about 40,000 cps at 20 RPM's and a slump of about 10 mm to about 27 mm wherein said gel comprises about 0.5 to about 20% by weight colloid.

4. The method of claim 3 which comprises preparing said gel to contain about 3 to about 10% colloid by weight.

* * * * *